United States Patent [19]
White et al.

[11] Patent Number: 5,920,643
[45] Date of Patent: Jul. 6, 1999

[54] FLEXIBLE LIGHTING ELEMENT CIRCUIT AND METHOD OF MANUFACTURING THE SAME

[75] Inventors: Timothy P. White, New Boston; Michael C. Messina, Goffstown, both of N.H.

[73] Assignee: Northeast Robotics LLC, Weare, N.H.

[21] Appl. No.: 08/857,712

[22] Filed: May 16, 1997

[51] Int. Cl.$^6$ .............................. G06K 9/00; F21V 21/00
[52] U.S. Cl. ............................................ 382/141; 362/249
[58] Field of Search .................................... 382/100, 141, 382/147, 152; 362/227, 249–250, 3, 173, 182; 348/86, 87; 385/901

[56] References Cited

U.S. PATENT DOCUMENTS

| | | | |
|---|---|---|---|
| 4,893,223 | 1/1990 | Arnold | 362/252 |
| 5,084,804 | 1/1992 | Schairer | 362/61 |
| 5,162,696 | 11/1992 | Goodrich | 313/511 |
| 5,172,005 | 12/1992 | Cochran et al. | 356/430 |
| 5,309,277 | 5/1994 | Deck | 362/237 |
| 5,404,282 | 4/1995 | Klinke et al. | 362/249 |
| 5,519,496 | 5/1996 | Borgert et al. | 356/394 |
| 5,585,783 | 12/1996 | Hall | 362/800 |
| 5,604,550 | 2/1997 | White | 396/429 |
| 5,722,760 | 3/1998 | Chien | 362/84 |

*Primary Examiner*—Leo H. Boudreau
*Assistant Examiner*—Bhavesh Mehta
*Attorney, Agent, or Firm*—Davis and Bujold

[57] ABSTRACT

An apparatus and method for forming a conical or domed ring light having a plurality of light sources arranged at a desired angle with respect to an optical axis. Some of the dimensions of the illumination apparatus are first determined and, then using the appropriate formulas, the remaining dimensions of the circuit board are calculated. Thereafter, the calculated dimensions are employed to cut, from a planar flexible circuit board, the desired arcuate section(s). The light sources are then installed at desired locations on a first surface of the flexible circuit board and are each coupled to a common electrical connector, having one or a plurality of power sources, to facilitate supplying electrical power to each one of the light sources. The circuit board is then folded into a conical or domed configuration, with the light sources facing inward, and each abutted end and lateral surfaces of the folded circuit board is suitably secured or fastened to one another to permanently retain the flexible circuit board in its folded state.

20 Claims, 6 Drawing Sheets

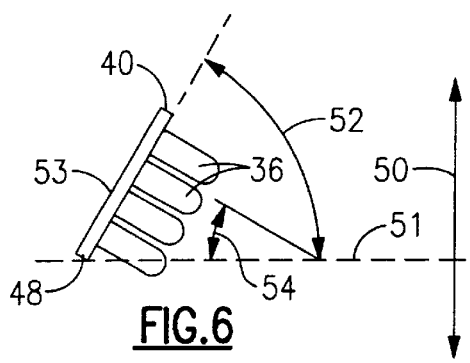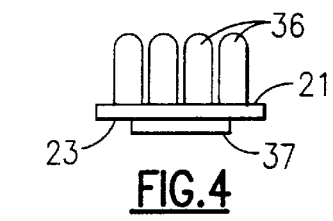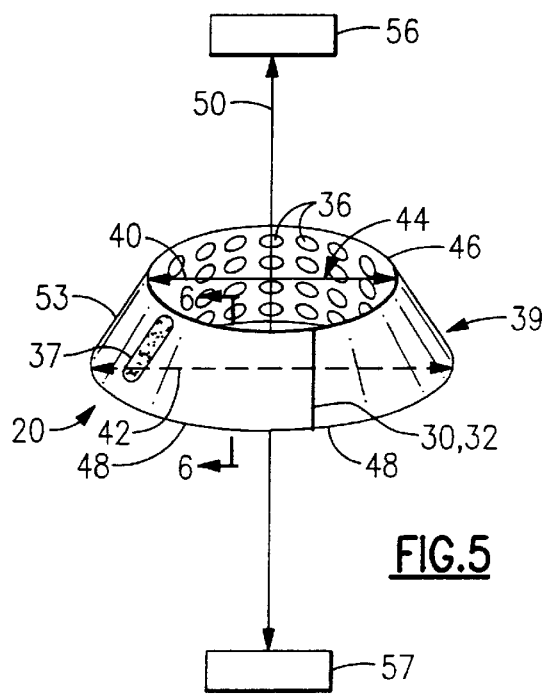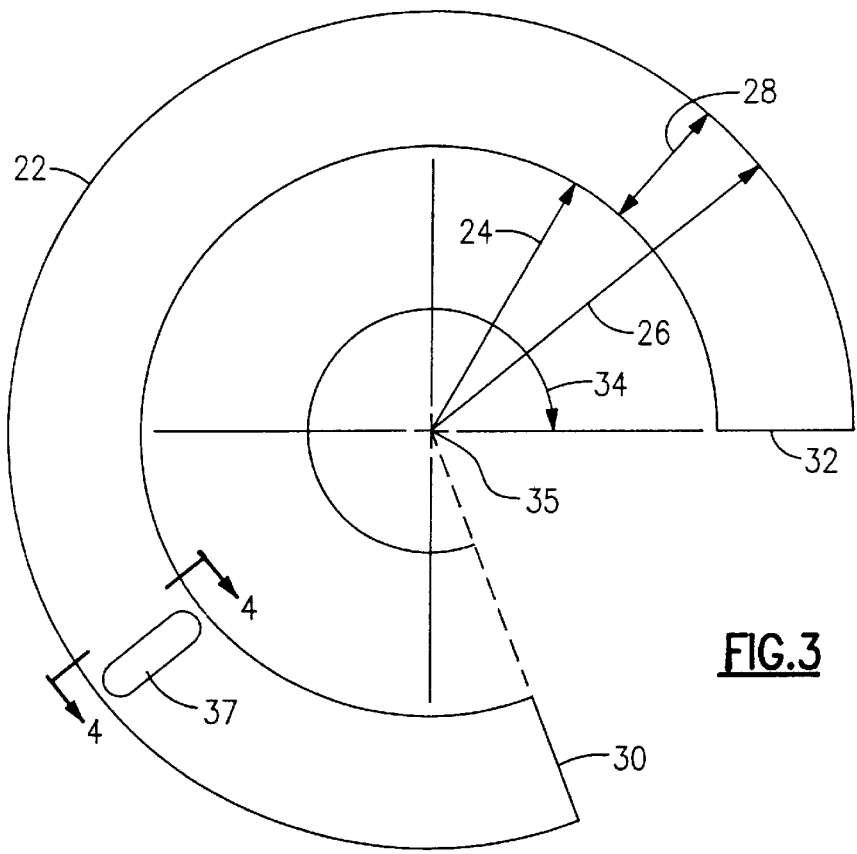

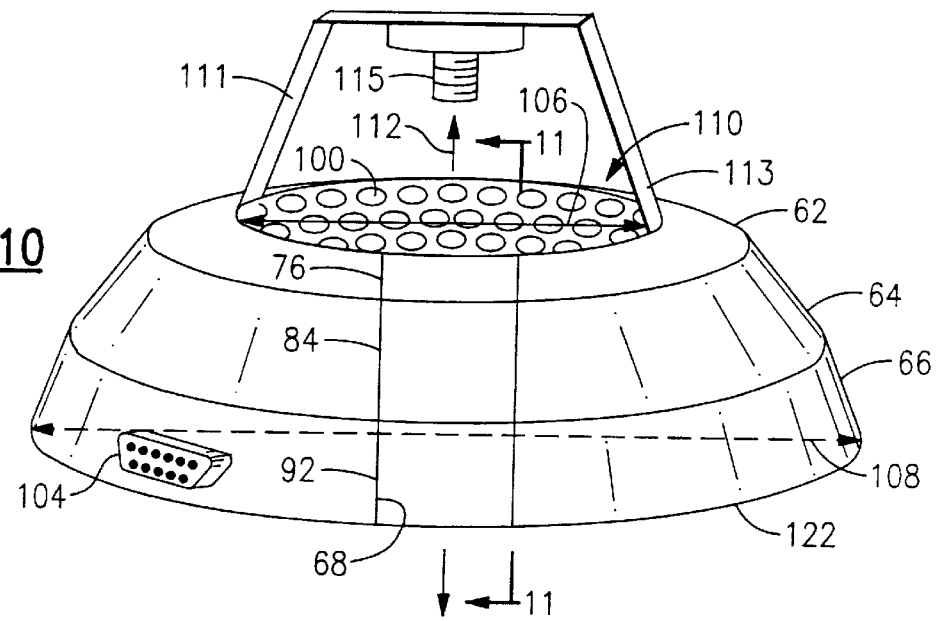

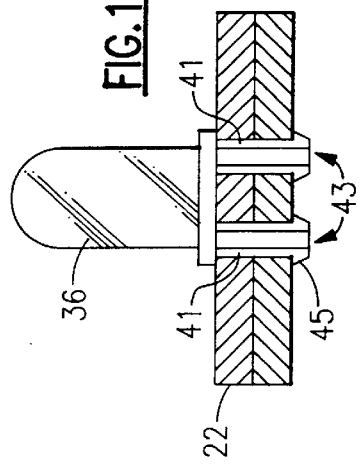
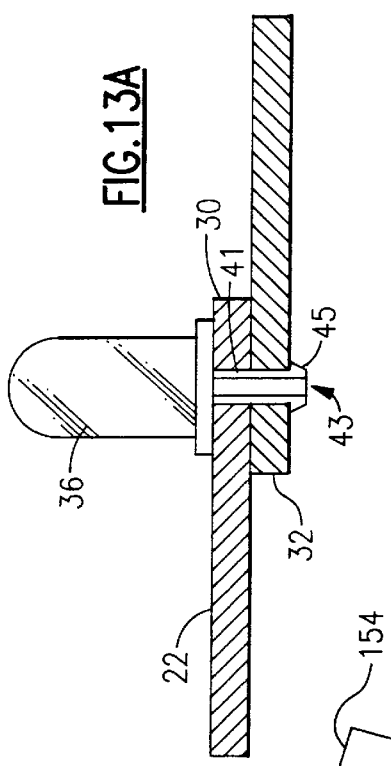
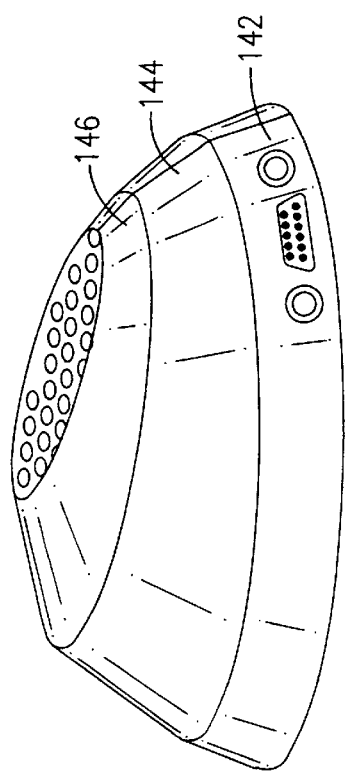
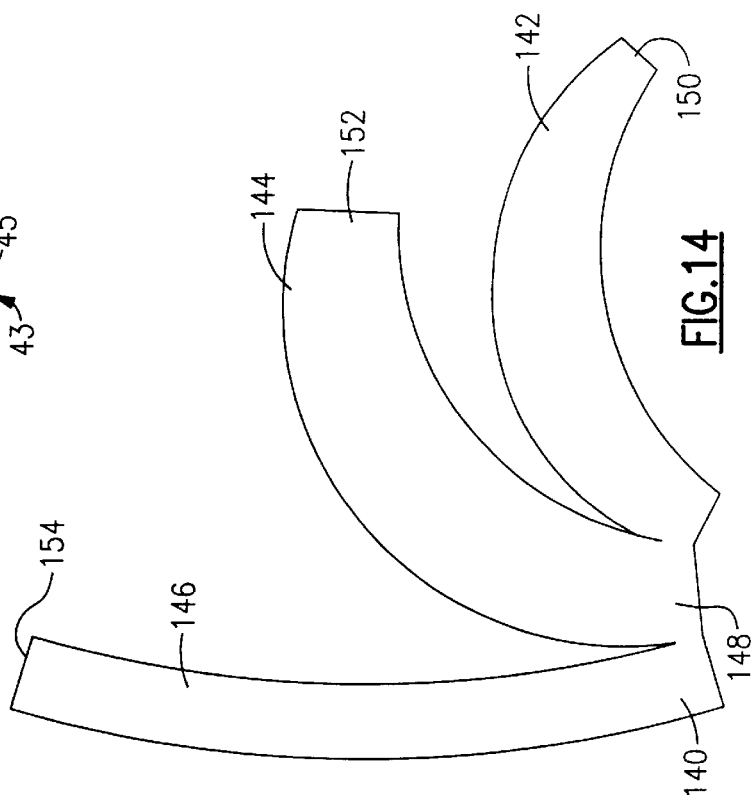

FLEXIBLE LIGHTING ELEMENT CIRCUIT AND METHOD OF MANUFACTURING THE SAME

FIELD OF THE INVENTION

This invention relates to a novel design for a conical or domed ring light and a method of manufacturing the same.

BACKGROUND OF THE INVENTION

When designing machine illumination systems, illumination geometry plays a key role in determining the quality of the image and the appearance of the object being observed. It is particularly true of highly specular objects and surfaces which reflect the lighting directly to the observer.

A machine vision engineer must select a lighting geometry which will cause the features of interest to be seen most clearly in the camera's field-of-view. Because specular objects reflect the lighting environment according to their own particular geometry, the selection of the lighting geometry for such applications is especially critical. For example, some applications require lighting from a "high angle", i.e. light supplied at a small angle relative to the optical axis, while other applications require illumination from a "low angle", i.e. light supplied at a much greater angle relative to the optical axis. It is advantageous for the machine vision engineer to have the greatest possible variety of illumination geometries available so as to be able to choose the ideal illumination geometry for any particular illumination application.

Many applications require a radially uniform lighting geometry so that the features of interest will be identically illuminated regardless of their orientation in the field-of-view. Currently, ring lights are available in only a limited variety of angles of incidence. For example, a fiberoptic ring light offers a narrow band of intense illumination with the direction of illumination typically being parallel to or nearly parallel to a central axis of the ring light. An angled reflector ring may be attached to the fiberoptic ring light source in order to redirect the illumination field at a different angle. For example, a ring reflector with a 45° inner reflecting surface immediately under the fiber ring illumination aperture will redirect the light inwardly toward and perpendicular to the central axis of the ring light, creating a "low angle dark field" illumination geometry.

A lighting element ring light consists of a number of light emitting diodes (LEDs) 2 located on a circuit board 4, typically in a circular array around a central aperture 6, as can be seen in FIG. 1. Due to automated manufacturing constraints, the lighting elements 2 must be mounted to a flat circuit board such that the illumination axis, of each mounted lighting element, is perpendicular to the surface of the circuit board 4 and parallel to the central axis A of the manufactured ring light. Alternatively, a long thin circuit board 8 may have a plurality of lighting elements 10 mounted thereon and then the long thin circuit board 8, with a pair of opposed straight lateral edges 12, is bent into a cylindrical shape, as can be seen in FIG. 2, such that the lighting elements are facing inward substantially perpendicular to the central axis A of the ring light.

Automated assembly of lighting elements on circuit boards requires that the lighting elements be placed perpendicular to the circuit board. When the lighting elements are required to project light at any angle other than substantially perpendicular to the circuit board, the lighting elements are individually bent to a desired angle, relative to the circuit board, by laborious hand assembly when the lighting elements are assembled in a fixture and a wiring harness is built up by hand to connect the leads in a desired circuit configuration. Such manual assembly greatly increases the manufacturing costs and reduces the reliability of the finished illumination product. It is desirable for the lighting element illumination circuit to be designed for assembly by a highly reliable automatic positioning and assembly machine in such a manner that the lighting elements can be oriented at any desired angle without intense hand labor.

SUMMARY OF THE INVENTION

Wherefore, it is an object of the present invention to overcome the aforementioned problems and drawbacks associated with the prior art designs.

Further object of the invention is to allow the design and fabrication of a circuit board carrying a plurality of light sources, such as an array of LEDs, using standard automated circuit board assembly techniques whereby the resulting light source has virtually any desired angle of incidence and a desired solid angle of illumination.

Further object of the invention is to design and fabricate a circuit board from a flat planar arcuately shaped member, or plurality of members having a common edge, each generally in the shape of the letter "C", and then mount the lighting elements perpendicular onto each accurately shaped member. After automated assembly and soldering, the arcuately-shaped circuit board is then formed or bent into a domed or conical section with the lighting elements facing inwardly.

Still another object of the invention is be able to select the width of the circuit board and the enclosed angle of the arcuately shaped circuit board, prior to final bending and forming, so that a desired angle of illumination and a desired solid angle illumination, relative to the central axis of the ring light, is attained.

Yet another object of the invention is to provide a method and an apparatus in which flexible arcuately shaped circuits, of different widths and shaped arcuate sections, may be designed and fabricated from a single unitary circuit board which can then have desired illumination sources placed thereon and, thereafter, be bent or folded up to form a dome member consisting of a multiplicity of integrally joined cylindrical, planar and/or conical sections. The plurality of arcuate sections can be powered by a single power source via a common bus, having one or a plurality of power sources, or, if desired, by a plurality of separate power sources.

Another object of the invention is to integrate other electrical components, such as strobe circuitry, an image analysis, or board-level camera mounting and control functions, etc., with the arcuately shaped circuit board(s), in addition to the lighting elements and their accompanying resistors, so that additional functions may be performed by the manufactured illumination source.

A still further object of the invention is to facilitate the manufacture of complex lighting geometries by utilization of standard automated circuit board assembly techniques and methods thereby facilitating low manufacturing costs and high production reliability.

The present invention relates to a circuit board for forming a conical-shaped ring light, said circuit board comprising a flexible, elongate member having opposed first and second exterior surfaces, and said circuit board having a pair of opposed end surfaces and a pair of lateral side surfaces; said first surface of said flexible circuit board supporting a plurality of individual light sources thereon; and said circuit board supporting an electrical bus, having at least one power source, which is connected to at least one of said plurality of individual light sources to facilitate connection of at least one of said plurality of individual light sources to a power source; wherein at least one of said pair of lateral side surfaces of said circuit board has an arcuate shape to facilitate formation of said flexible circuit board into a conical ring light configuration which has a central opening extending therethrough.

The present invention also relates to a method of forming a conical-shaped ring light from a flexible circuit board, said method comprising the steps of: cutting a circuit board from a flexible, elongate member, said circuit board having opposed first and second exterior surfaces and having a pair of opposed end surfaces and a pair of lateral side surfaces, and at least one of said pair of lateral side surfaces of said circuit board has an arcuate shape to facilitate formation of said flexible circuit board into a conical ring light configuration; placing a plurality of individual light sources on said first surface of said flexible circuit board; connecting an electrical bus, having one at least one power source, to said circuit board; interconnecting at least one of said plurality of individual light sources to said electrical bus to facilitate connection of at least one of said plurality of individual light sources to said at least one power source; and forming said flexible circuit into a conical ring light configuration with said plurality of individual light sources facing inward.

BRIEF DESCRIPTION OF THE DRAWINGS

The invention will now be described, by way of example, with reference to the accompanying drawings in which:

FIG. 3 is a diagrammatic top plan view of an arcuate flexible circuit used to manufacture a conical or domed ring light according to one embodiment of the present invention;

FIG. 4 is a diagrammatic cross-sectional view along section line 4—4 of FIG. 3;

FIG. 5 is a diagrammatic perspective view showing the assembled conical or domed shape of the flexible circuit of FIG. 3;

FIG. 6 is a diagrammatic partial cross sectional view, along section line 6—6 of FIG. 5, of the formed domed ring light;

FIG. 9 is a diagrammatic cross-sectional view, along section line 9—9 of FIG. 8, of the flexible circuit;

FIG. 10 is a diagrammatic perspective view showing the assembled state of the domed ring light of FIG. 7;

FIG. 11 is a diagrammatic partial cross-sectional view, along section line 11—11 of FIG. 10, of the formed complex conical or domed ring light;

FIG. 13A is a diagrammatic partial cross-sectional view showing the overlapped engagement between opposed ends of a flexible circuit;

FIG. 13B is a diagrammatic partial cross-sectional view showing an overlapped engagement between two overlap portions of a flexible circuit;

FIG. 14 is a diagrammatic top plan view of a third embodiment of a flexible circuit used to manufacture a conical or domed ring light according to the present invention; and FIG. 15 is a diagrammatic perspective view showing the assembled conical or domed shaped of the flexible circuit of FIG. 14.

DESCRIPTION OF THE PREFERRED EMBODIMENTS

Figure 1:
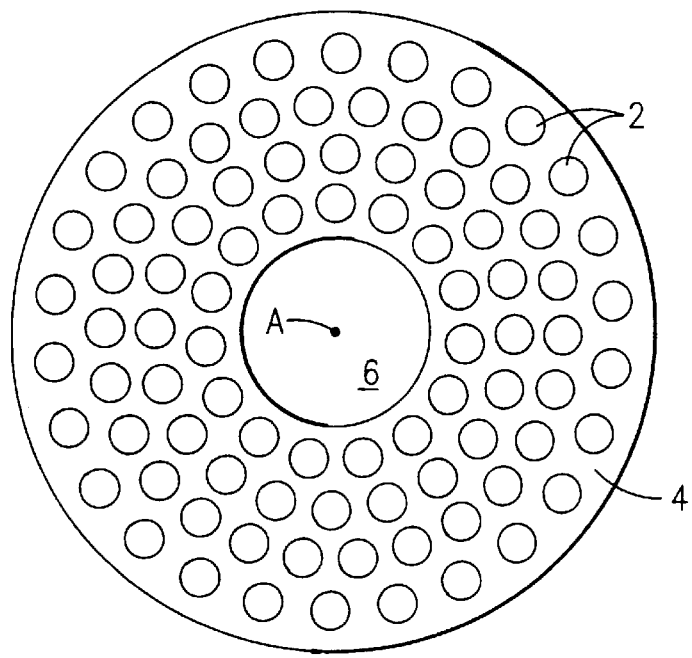
FIG. 1 is a diagrammatic plan view of a flat prior art ring light having an array of lighting elements located about a central aperture.
Figure 2:
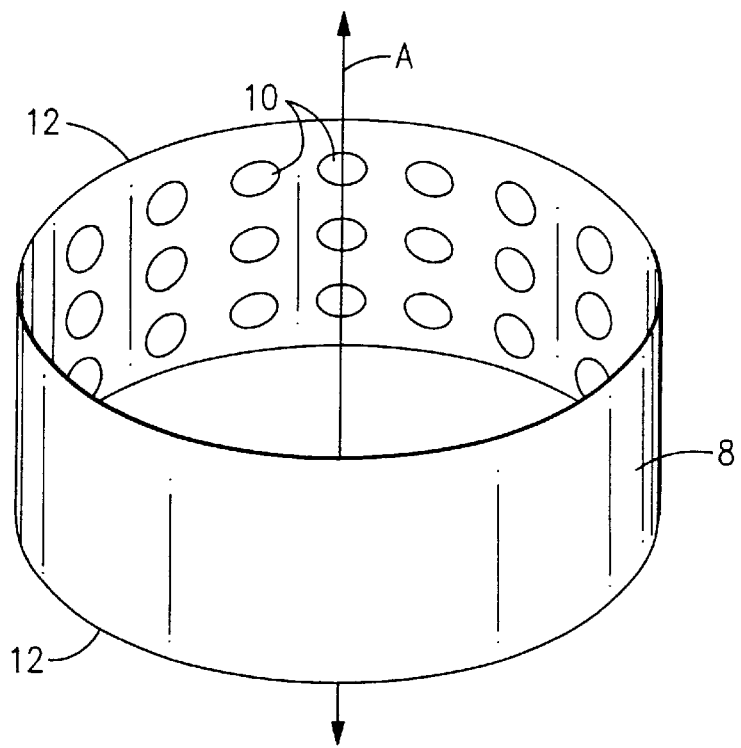
FIG. 2 is a diagrammatic perspective view of a prior art ring light formed from an elongate circuit board, having a plurality of lighting elements placed thereon, and bent into a cylindrical shape.

Turning now to FIGS. 3–6, a detailed description concerning a first embodiment of the present invention will now be provided. As can be seen in those Figures, a domed ring light 20 is formed from a flat flexible circuit board 22 having an arcuate shape which is depicted in FIG. 3.

The flat flexible circuit 22 has an inner radius 24 and an outer radius 26, measured from center point 35, with the difference between those two radii defining a width of the flexible circuit or a segment width 28. The flexible circuit 22 has a pair of opposed ends comprising a first end surface 30 and a second end surface 32. Each surface has a width which is equal to the segment width of the flexible circuit 22. A flat arc solid angle 34, measured in degrees from the first end surface 30 to the second end surface 32 about a center point 35, is defined by the arcuate flexible circuit 22.

The segment width 28 of the flexible circuit 22 is selected such that a desired number of LEDs or lighting elements 36, or other desired illuminating members, can be spaced across the width of the flexible circuit 22, while the length is selected such that a desired number of lighting elements 36 can be spaced along the length of the flexible circuit 22. The lighting elements 36 are mounted perpendicular, or at some other desired orientation, with respect to the flexible circuit 22, by conventional automated assembling and soldering techniques, prior to further processing of the flexible circuit 22.

FIG. 4 depicts the installed position of the lighting elements 36 on a second exterior surface 21 of the flexible circuit 22. Once all of the installed lighting elements 36 are electrically coupled to a common bus 37, having one or a plurality of power sources, located on a first exterior surface 23 by conventional electrical circuitry, not shown in detail, to facilitate powering of some or all of the lighting elements 36 by a single power source or multiple power sources or circuits, the flexible circuit 22 is then ready for bending or forming into a conical or domed configuration 39 (FIG. 5).

As can be seen in FIG. 5, the flat flexible circuit 22 of FIG. 3 is bent into a conical or domed configuration 39 with all of the installed lighting elements 36 facing inward and the common bus 37, having one or a plurality of power sources, typically facing outward. Although the remainder of this patent application depicts and refers to the common bus 37 as facing outward in the finally assembled configuration, it is to be appreciated that the common bus may be located in a variety of different orientations. For example, common bus 37 may face inward, i.e. be located on the inwardly facing surface, may be located along an edge of the flexible circuit or possibly located between the two exterior surfaces of the flexible circuit, e.g. the common connector may be located or supported by an intermediate layer forming the flexible circuit. Accordingly, although the common bus will hereafter be indicated as being located on the outwardly facing surface, such reference is also intended to cover positioning of the common bus anywhere on or within the flexible circuit, i.e. on an inwardly facing surface, on an outwardly facing surface, along an edge of the flexible circuit or on an intermediate layer forming the flexible circuit.

The first end surface 30 of the flexible circuit 22 is brought into abutment with and aligned with the second end surface 32 of the flexible circuit 22. Once the flexible circuit 22 is in this position, the abutted end surfaces 30, 32 of the flexible circuit 22 can be permanently secured to one another by an adhesive or some other conventional attaching or securing mechanism or means. In this assembled state, the conical or domed configuration 39 defines an upper edge diameter 40 and a lower edge diameter 42 with a central opening 44 extending therebetween.

Alternatively, it is to be appreciated that the two opposed ends of the flexible circuit 22 can overlap one another. For example, as can be seen in FIG. 13A, one lighting element 36 can be supported on a surface adjacent one end 30 of the flexible circuit 22 by an elongate lead 41 extending through the surface. The elongate lead 41 has a length that is approximately twice the thickness of the flexible circuit 22. Accordingly, the elongate lead 41 allows the second opposed end 28 of the elongate circuit, which is provided with an aperture 43 therein, to receive the lead 41 and maintain the two opposed ends 30, 32 of the flexible circuit 22 in an overlapped abutting relationship. If desired, the end portion of the lead 41, which passes through the second opposed end of the flexible elongate circuit, can be provided with a mechanism 45, e.g. a tapered annular lip which readily allows the aperture 43 to pass therethrough, to prevent the two overlapped ends 30, 32 from being disconnected from one another. Such arrangement will maintain the two overlapped ends 30, 32 in abutting relationship and prevent undesired disassembly of the conical or domed configuration.

FIG. 13B shows a second embodiment, similar to that of FIG. 13A, in which a pair of leads 41 pass through a pair of mating apertures 43 provided in the overlap portion of the flexible circuit 22 to retain the two overlapped portions of the flexible circuit in an abutting relationship and thereby prevent undesired disassembly of the formed conical or domed configuration. As this embodiment is very similar to the previous embodiment of FIG. 13A, a further detailed discussion concerning the same is not provided.

The domed configuration 39 also defines a first upper lateral edge circumference 46 and a second lower lateral edge circumference 48. The central opening 44 of the domed configuration 39 is positioned, during use, near or along an optical axis 50 extending between an observation device 56 and an object to be observed 57 to provide the desired illumination effect.

An acute segment angle 52 (FIG. 6) is defined by a horizontal plane 51, extending coincident with and parallel to the second lateral edge circumference 48 of the domed configuration, and a side surface 53 of the domed configuration 39. An angle of incidence 54, of the light to be supplied by the formed domed ring light, is a complimentary angle with the segment angle 52, i.e. the combination of the acute segment angle 52 and the angle of incident 54 of the light equals 90 degrees.

The machine vision engineer needs the ability to preselect the segment width 28 and the segment angle 52 so as to achieve the ideal illumination geometry for any particular illumination application. It is to be noted that the shape of the illumination light source is critical in achieving the desired width of the illumination field as well as the desired angle of incidence 54 relative to the optical axis 50.

It is to be appreciated that the angle of incidence 54 can vary from application to application. For any given application, the machine vision engineer first determines the required illumination conditions and then designs an appropriate illumination source by using a series of equations. Accurate inputs are critical in determining the flat arc solid angle 34 so as to obtain the desired angle of incidence 54 relative to the optical axis 50. As will be apparent from the description that follows, it is possible to readily obtain a desired angle of incident 54 for a variety of illumination applications while still using conventional automated manufacturing techniques to mount the light sources, e.g. lighting elements, to the flexible circuit 22.

By using appropriate inputs, representing the desired conditions for the segment width 28 and the segment angle 52, one can design a conical or domed ring light 20 which achieves the desired lighting affect. The necessary inputs are the: 1) segment width 28 (typically in inches or millimeters), 2) the segment angle 52 (typically in degrees), and 3) the lower edge diameter 42 (typically in inches or millimeters). From these values, it is possible to calculate the Inner Flat Radius (IFR) 24, the Outer Flat Radius (OFR) 26 and the Flat Arc Solid Angle (FASA) 34.

The following formulas are used to calculate the various dimensions for forming a conical or domed ring light according to the present invention:

$$\text{Assembled Upper Edge Diameter (AUED)} = (LD) - (2)(SW)(\cos B) \quad (1)$$

where,

LD equals the lower diameter of the domed configuration;

B equals the segment angle; and

SW is the segment width of the flat flexible circuit board.

The assembled upper and lower edge circumferences are calculated as follows:

$$\text{Assembled Lower Edge Circumference } (C) = (LD)(\pi) \quad (2)$$

where,

LD equals the lower edge diameter of the domed configuration; and $$\text{Assembled Upper Edge Circumference } (c) = (AUED)(\pi) \quad (3)$$

where,

AUED equals the assembled upper edge diameter of the domed configuration.

The Inner Flat Radius (IFR) is calculated as follows:

$$\text{Inner Flat Radius (IFR)} = (c)(SW)/(C-c) \quad (4)$$

where,

C is the assembled lower edge circumference of the domed ring light;

c is the assembled upper edge circumference of the domed ring light; and

SW is the segment width of the flat flexible circuit board.

The Outer Flat Radius (OFR) is calculated as follows:

$$\text{Outer Flat Radius (OFR)} = (IFR) + (SW) \quad (5)$$

where,

IFR equals the inner flat radius of the flat flexible circuit board; and

SW is the segment width of the flat flexible circuit board.

To calculate the flat arc solid angle, the following formula is utilized:

Flat Arc Solid Angle (FASA)=(Outer Arc Length)(360°)/
(2π)(OFR)     (6) this formula simplifies to:

Flat Arc Solid Angle (FASA)=(IFR)(c)/(2)(π)     (7)

where,

IFR is inner flat radius of the flat flexible circuit; and c is the assembled upper edge circumference of the domed configuration.

Once the inner flat radius (IFR), the outer flat radius (OFR) and the flat arc solid angle (FASA) are determined, these dimensions can be marked or scribed on a surface of a suitable flexible circuit or entered into the control program used by the automatic assembly machine to fabricate the circuit. Thereafter, the flexible circuit is cut out along the marked or scribed dimensions to form the arcuate section shown in FIG. 3. Next, the lighting elements 36 are applied to a first surface 21 of the flexible circuit 22 and the common bus 37, having one or a plurality of power sources, is attached to the second opposite surface 23. All the lighting elements 36 are then connected to the common bus 37, having one or a plurality of power sources, by electrical circuitry. Finally, the fully populated circuit is formed or bent into the conical or domed configuration shown in FIG. 5.

It is to be appreciated that the above formulas can be used to produce a variety of different configurations. For example, as can be seen in FIGS. 7 through 11, 14 and 15, complex conical or domed configurations, having three (3) different segment angles, can be manufactured and the production of these designs will now be described in further detail.

Figure 7:
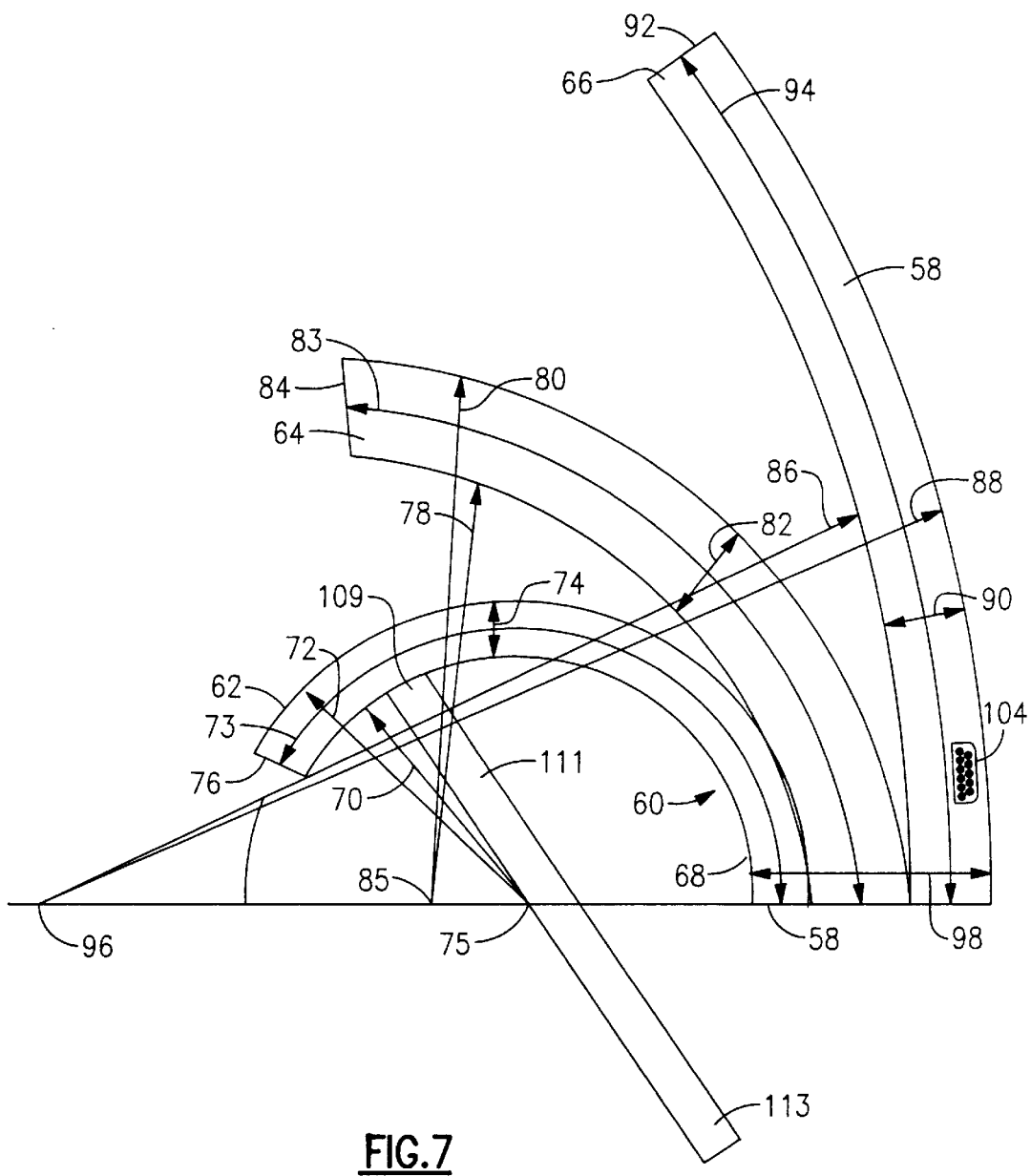
FIG. 7 is a diagrammatic plan view of a second embodiment of a flexible circuit used to manufacture a domed ring light according to the present invention.

As can be seen in FIG. 7, a flat flexible circuit 60 is employed. This circuit has three (3) arcuate sections 62, 64, 66 which are all integrally connected with one another along a common end surface 68.

The first inner arcuate section 62 has an inner radius 70 and an outer radius 72 with the difference between these two radii defining a section width 74 of the first arcuate section 62. The first arcuate section 62 has an opposed end surface 76 which is located opposite to the common end surface 68. The first arcuate section 62 also defines a flat arc solid angle 73, measured in degrees from the common end surface 68 to the opposed end surface 76 about a center point 75.

The second intermediate arcuate section 64 has an inner radius 78 and an outer radius 80 with the difference between these two radii defining a section width 82 of the second intermediate arcuate section 64. The second intermediate arcuate section 64 has an opposed end surface 84 which is located opposite to the common end surface 68. The second intermediate arcuate section 64 also defines a flat arc solid angle 83, measured in degrees from the common end surface 68 to the opposed end surface 84 about a center point 85.

The third outer arcuate section 66 has an inner radius 86 and an outer radius 88 with the difference between these two radii defining a section width 90 of the third outer arcuate section 66. The third outer arcuate section 66 has an opposed end surface 92 which is located opposite to the common end surface 68. The third outer arcuate section 66 also defines a flat arc solid angle 94, measured in degrees from the common end surface 68 to the opposed end surface 92 about a center point 96.

The combined width of the three end surfaces 76, 84, 92 is equal to the width of the common end surface 68 and also equal to the total segment width 98 of the complex domed configuration. As with the previous embodiment, each section width 74, 82, and 90 is selected such that a desired number of lighting elements 100 (FIG. 8) can be spaced across the width of each one of the three arcuate sections 62, 64, 66.

Once all of the lighting elements 100 are positioned on a first surface 102 of the flexible circuit board 58 and electrically coupled to a common bus 104, having one or a plurality of power sources, located on the other side, the flexible circuit 58 is then bent or formed into the complex conical or domed configuration (FIG. 10) with all of the installed lighting elements 100 facing inwardly and the common bus, having one or a plurality of power sources, 104 facing outward. As can be seen in FIG. 10, the flexible circuit 58 is bent into the complex conical or domed configuration so that the common end surface 68 is brought into engagement with and aligned with the three opposed longitudinal edges 76, 84 and 92. once in this position, the abutted edges 68 and 76, 84, 92 and the adjacent lateral edges can be permanently secured to one another by an adhesive or some other conventional attachment or securing mechanism or means, e.g. see FIGS. 13A and 13B for example. The formed domed configuration defines an upper diameter 106 and a lower edge diameter 108 with a central opening 110 extending therethrough. As with the previous embodiment, the central opening 110 of the illumination source is position, during use, along the optical axis 112 to provide the desired illumination effect to an object to be observed.

It is to be appreciated that the flexible circuit 60 may be provided with a further segment 111 for an inspection device or some other desired component or member. One end 109 of the further segment 111 is either attached or integrally formed with an inner radiused portion of the first inner arcuate section 62 while the opposite end 113 of the further segment 111 is unattached. Once the flexible circuit is fully populated and then bent into the complex conical or domed configuration, the further segment 111 is bent into the configuration shown in FIG. 10 and the free, unattached end 113 of further segment 111 is glued or otherwise permanently affixed to an upper edge of the conical or domed configuration by a conventional attachment mechanism. Thereafter, the further segment 111 can be used to support an observation device 115, for example, or any other desired component.

Although not specifically shown in the drawings, the further segment 111 is provided with one or more electrical wires or leads which are either coupled to the common bus 37, to facilitate powering of the optical or electrical component or device supported by the flexible segment 111, or directly coupled to a completely separate power source, if desired. Further, it is to be appreciated that the further segment or segments 111 can have a variety of different shapes and/or configuration so that a plurality of desired components and/or devices can be supported thereon, e.g. any desired optical or electrical device or component, a camera, an illumination element(s), etc. As the shape and/or configuration of the further segment 111 can vary from application to application and would be readily apparent to one skilled in the art, a further detail description or discussion concerning such variations is not provided.

As can be seen in FIG. 11, each one of the three arcuate sections 62, 64, 66 defines an acute segment angle 118, 116, 114, respectively, between a horizontal plane 120, extending parallel to and coincidence with second lateral edge circumference 122 of the complex domed configuration, and a side surface 124, 126, 128, respectively, of the complex domed configuration. As with the previous embodiment, an angle of incidence of the light, to be supplied by the formed complex domed ring light, is a complementary angle to the formed segment angles 114, 116, 118.

As with the previous embodiment, the required input data are: (1) the segment width 90 of the outer arcuate section 66

(typically in inches or millimeters), (2) the segment angle 114 of the outer arcuate section 66, and (3) the lower edge diameter 108 of the outer arcuate section 66 (typically in inches or millimeters). From these inputs, the Inner Flat Radius 86 of the outer arcuate section 66, the Outer Flat Radius 88 of the outer arcuate section 66 and the Flat Solid Angle 94 of the outer arcuate section 66 are then calculated by formulas (1) through (5) and (7) above.

After these calculations are performed, the dimension of the Inner Flat Radius 86 of the outer arcuate section 66 is then doubled and used as the lower diameter (LD) of the intermediate arcuate section 64. This input is utilized with the segment angle 116 of the intermediate arcuate section 64 (typically in degrees) and the segment width 82 of the intermediate arcuate section 64 (typically in inches or millimeters) to calculate the remaining dimensions of the intermediate arcuate section 64. Formulas (1) through (5) and (7) above are used to calculate ultimately the Inner Flat Radius 78, the Outer Flat Radius 80 and the Flat Arc Solid Angle 83 of the intermediate arcuate section 64.

Once these calculations are performed, the dimension of the inner flat radius 78 of the intermediate arcuate section 64 is then doubled and used as the lower diameter (LD) of the inner arcuate section 62. This input is utilized with the segment angle 118 of the inner arcuate section 62 (typically in degrees) and the segment width 74 of the inner arcuate section 62 (typically in inches or millimeters) to calculate the remaining dimensions of the inner arcuate section 62. Formulas (1) through (5) and (7) above are used to calculate ultimately the Inner Flat Radius 70, the Outer Flat Radius 72 and the Flat Arc Solid Angle 73 of the inner arcuate section 62.

The above calculation procedure, from the outer most arcuate section to the inner most arcuate section, continues until the dimensions for each one of the arcuate sections is calculated.

Figure 12:
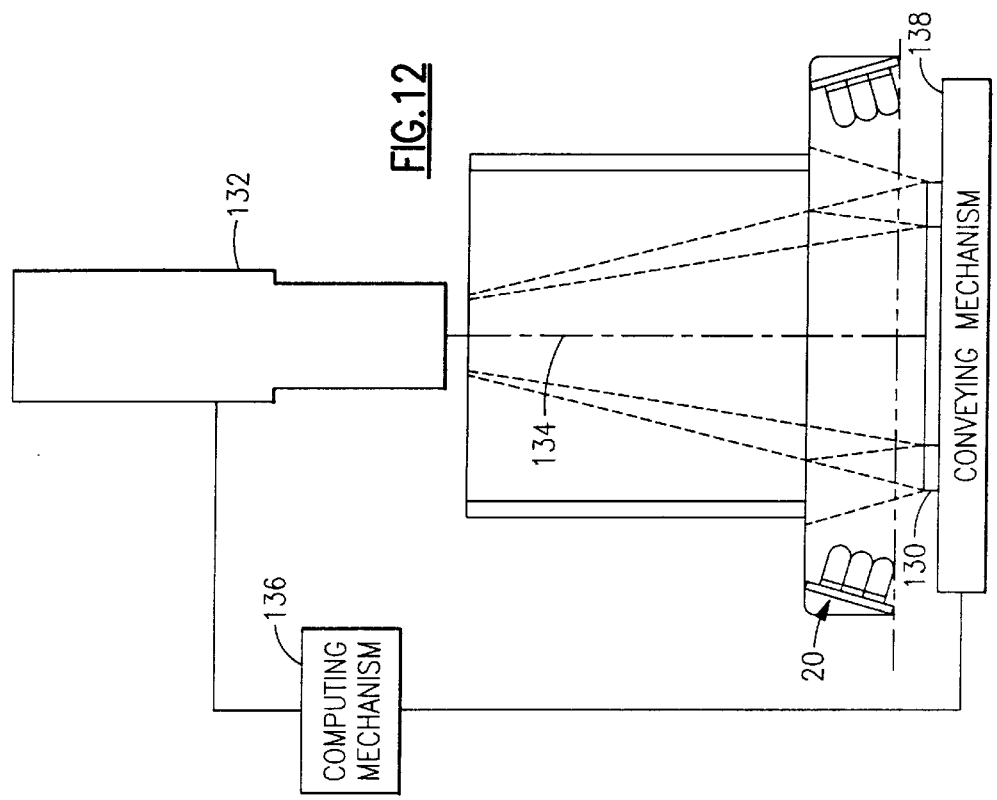
FIG. 12 shows one use of the conical or domed ring light according to the present invention.
Figure 8:
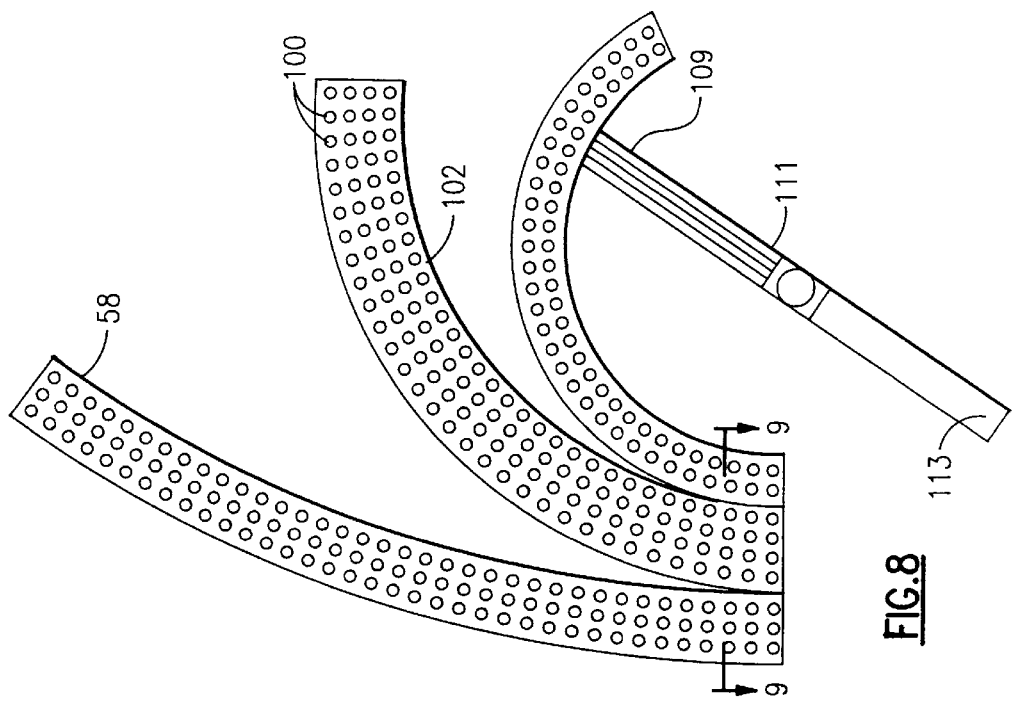
FIG. 8 is a diagrammatic bottom plan view of the flexible circuit of FIG. 7.

One possible application of the domed ring light 20, according to the present invention, can be seen in FIG. 12. As shown in this Figure, the ring light 20 has a desired angle of incident with respect to the object to be observed 130 by an observation device 132, such as a camera along observation axis 134. The sensed image is then used to control further processing of the object to be observed 130 or other component being inspected or imaged by the observation device 132. For example, the sensed image may be conveyed to a computing means or mechanism 136 where the sensed image is used in combination with a known algorithm to determine a desired feature or attribute of the object to be observed 130. The computing means or mechanism 136 then sends an appropriate control signal to a conveyor means or mechanism 138 which controls further manipulation or processing of the object to be observed 130 or other component being inspected or imaged. As the present invention relates merely to the illumination source, and does not specifically relate to the observation device 132, the computing means 136 or conveying means 138, a further detail discussion concerning those known features or components is not provided herein.

Turning now to FIGS. 14 and 15, a brief description concerning a third embodiment of the present invention will now be discussed. According to this embodiment, the flexible circuit 140 comprises a first arcuate segment 142, a second arcuate segment 144 and a third arcuate segment 146 which are all connected to one another and integrally formed with a common end portion 148. The first arcuate segment 142 has an opposed end 150, the second arcuate segment 144 has an opposed end 152 and the third arcuate segment 146 has an opposed end 154.

The width of the first and the second arcuate segments 142, 144 vary along the length of those two arcuate segments while the width of the third arcuate section 146 is constant along its length. As a result of the varying widths, the aperture 156 which is formed in the resulting domed configuration 158 is located off-center from a central axis.

It is to be appreciated that a variety of different arrangements and configurations can be utilized employing the teaching of the present invention. Further, the flexible circuits can include tabs, holes, connectors and other mechanical and electrical features to facilitate fabrication and assembly of the formed domed configuration. Typically, the plurality of individual light sources will have an angle of incident, with respect to the optical axis, of between about 2.5° to about 87.5°.

The term "arcuate shape" surface, as used herein and in the claims, means a surface or combination of sequentially arranged surfaces which do not lie in a single plane. That is, the single surface or sequentially arranged surfaces are curved, bent, or otherwise nonlinear to facilitate formation of a substantially conical or domed configuration.

Since certain changes may be made in the above described conical or domed ring light and method, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, we claim:

1. A circuit board for forming a conical-shaped ring light, said circuit board comprising a flexible, elongate member having opposed first and second exterior surfaces, and said circuit board having a pair of opposed end surfaces and a pair of lateral side surfaces;

said first exterior surface of said flexible circuit board supporting a plurality of individual light sources thereon; and said circuit board supporting an electrical bus, having at least one power source, which is connected to at least one of said plurality of individual light sources to facilitate connection of at least one of said plurality of individual light sources to a power source;

wherein at least one of said pair of lateral side surfaces of said circuit board has an arcuate shape to facilitate formation of said flexible circuit board into a conical ring light configuration which has a central opening extending therethrough.

2. A circuit board according to claim 1, wherein each of said pair of lateral side surfaces of said circuit board has an arcuate shape to facilitate formation of said flexible circuit board into a conical ring light configuration.

3. A circuit board according to claim 1, wherein said electrical bus, having at least one power source, is a common electrical bus which is connected to each one of said plurality of individual light sources to facilitate connection of each of said plurality of individual light sources to said at least one power source.

4. A circuit board according to claim 3, wherein a lead of at least one of said plurality of individual light sources maintains said opposed end surfaces of said flexible circuit in an abutting partially overlap relationship with one another.

5. A circuit board according to claim 1, wherein said circuit board has a plurality of arcuate sections and each of said plurality of arcuate sections are integrally formed with said common end surface.

6. A circuit board according to claim 5, wherein each of said plurality of arcuate sections has a different flat arc solid angle.

7. A circuit board according to claim 1, wherein an angle of incident of each of said plurality of individual light sources ranges from about 2.5 degrees to about 87.5 degrees.

8. A circuit board according to claim 1, wherein said opposed end surfaces of said flexible circuit one of abut against and partially overlap one another and are secured to one another by an attachment mechanism.

9. A circuit board according to claim 1, wherein after formation of said flexible circuit board into a conical ring light configuration, each one of said plurality of individual light sources, which forms a portion of an illumination field of the object to be observed, faces inward.

10. A circuit board according to claim 1, when formed into a conical ring light configuration, in combination with an imaging device which is electrically coupled to a computing mechanism, and a conveying mechanism which is electrically coupled to said computing mechanism, and said imaging device supplies a sensed image, of the object to be imaged, to said computing mechanism which determines a desired feature of said object to be observed and outputs a signal to said conveying mechanism to control further manipulation of said object to be observed based upon the determined feature.

11. A method of forming a conical-shaped ring light from a flexible circuit board, said method comprising the steps of:

cutting a circuit board from a flexible, elongate member, said circuit board having opposed first and second exterior surfaces and having a pair of opposed end surfaces and a pair of lateral side surfaces, and at least one of said pair of lateral side surfaces of said circuit board has an arcuate shape to facilitate formation of said flexible circuit board into a conical ring light configuration;

placing a plurality of individual light sources on said first surface of said flexible circuit board;

connecting an electrical bus, having one at least one power source, to said circuit board;

interconnecting at least one of said plurality of individual light sources to said electrical bus to facilitate connection of at least one of said plurality of individual light sources to said at least one power source; and forming said flexible circuit into a conical ring light configuration with said plurality of individual light sources facing inward.

12. A method according to claim 11, further comprising the step of providing each of said pair of lateral side surfaces of said circuit board with an arcuate shape to facilitate formation of said flexible circuit board into a conical ring light configuration.

13. A method according to claim 11, further comprising the step of permanently securing at least some adjacent and overlapped end surfaces and side surfaces to maintain said at least some adjacent and overlapped surfaces in a desired location to permanently form said conical ring light configuration.

14. A method according to claim 11, further comprising the step of providing a plurality of arcuate sections and integrally forming each of said plurality of arcuate sections with a common end surface.

15. A method according to claim 11, further comprising the step of providing a common electrical bus which is connected to each one of said plurality of individual light sources to facilitate connection of each of said plurality of individual light sources to said at least one power source.

16. A method according to claim 11, further comprising the step of providing each of said plurality of arcuate sections with a different flat arc solid angle.

17. A method according to claim 11, further comprising the steps of selecting a desired segment width for each arcuate section, a desired segment angle for each said arcuate section, and a desired lower edge diameter for a lower most arcuate section, and calculating an inner flat radius for each said arcuate section, an outer flat radius for each said arcuate section, and a flat arc solid angle for each said arcuate section.

18. A method according to claim 11, further comprising the steps of using said conical ring light configuration in combination with an imaging device which is electrically coupled to a computing mechanism, and electrically coupling a conveying mechanism to said computing mechanism, and supplying a sensed image, of the object to be imaged, from said imaging device to said computing mechanism to determine a desired feature of said object to be observed and outputting a signal to said conveying mechanism to control further manipulation of said object to be observed based upon the determined feature.

19. A method according to claim 11, further comprising the steps of utilizing a lead of at least one of said plurality of individual light sources to maintain said opposed end surfaces of said flexible circuit in an abutting partially overlap relationship with one another.

20. A method according to claim 11, further comprising the steps of using said conical ring light configuration, in combination with an imaging device;

electrically coupling said imaging device to a computing mechanism;

electrically coupling said computing mechanism to a conveying mechanism; and supplying a sensed image, of the object to be imaged, via said imaging device to said computing mechanism which determines a desired feature of an object to be observed and outputs a signal to said conveying mechanism to control further manipulation of said object to be observed based upon the determined feature.

* * * * *